United States Patent [19]
Daugman

[11] Patent Number: 5,291,560
[45] Date of Patent: Mar. 1, 1994

[54] BIOMETRIC PERSONAL IDENTIFICATION SYSTEM BASED ON IRIS ANALYSIS

[75] Inventor: John G. Daugman, Huntingdon, England

[73] Assignee: Iri Scan Incorporated, Mt. Laurel, N.J.

[21] Appl. No.: 729,638

[22] Filed: Jul. 15, 1991

[51] Int. Cl.$^5$ .............................................. G06K 9/00
[52] U.S. Cl. ........................................ 382/2; 351/206; 354/62; 382/6; 382/30
[58] Field of Search ............................. 382/2, 6, 30, 9; 351/206, 221, 208, 205; 354/62; 364/413.01; 340/825.34

[56] References Cited

U.S. PATENT DOCUMENTS

| | | | |
|---|---|---|---|
| 4,109,237 | 8/1978 | Hill | 382/2 |
| 4,620,318 | 10/1986 | Hill | 382/2 |
| 4,641,349 | 2/1987 | Flom et al. | 382/2 |
| 5,016,282 | 5/1991 | Tomono et al. | 382/2 |

Primary Examiner—Joseph Mancuso
Attorney, Agent, or Firm—John P. McGonagle

[57] ABSTRACT

A system for rapid and automatic identification of persons, with very high reliability and confidence levels. The iris of the eye is used an optical fingerprint, having a highly detailed pattern that is unique for each individual and stable over many years. Image analysis algorithms find the iris in a live video image of a person's face, and encode its texture into a compact signature, or "iris code." Iris texture is extracted from the image at multiple scales of analysis by a self-similar set of quadrature (2-D Gabor) bandpass filters defined in a dimensionless polar coordinate system. The sign of the projection of many different parts of the iris onto these multiscale quadrature filters, determines each bit in an abstract (256-byte) iris code. The degrees-of-freedom in this code are based on the principle forms of variation in a population of irises studied. Because of the universal mathematical format and constant length of the iris codes, comparisons between them are readily implemented by the Exclusive-OR (XOR) logical operation. Pattern recognition is achieved by combining special signal processing methods with statistical decision theory, leading to a statistical test of independence based on a similarity metric (the Hamming distance) that is computed from the XOR of any two iris codes. This measure positively establishes, confirms, or disconfirms, the identity of any individual. It also generates an objective confidence level associated with any such identification decision.

21 Claims, 12 Drawing Sheets

| HD Criterion | Odds of False Accept | Odds of False Reject |
|---|---|---|
| 0.25 | 1 in 13.5 billion | 1 in 1,490 |
| 0.26 | 1 in 2.04 billion | 1 in 2,660 |
| 0.27 | 1 in 339 million | 1 in 4,850 |
| 0.28 | 1 in 60 million | 1 in 9,000 |
| 0.29 | 1 in 12 million | 1 in 17,100 |
| 0.30 | 1 in 2.4 million | 1 in 32,800 |
| 0.31 | 1 in 603,000 | 1 in 64,200 |
| 0.32 | 1 in 151,000 | 1 in 128,000 |
| 0.33 | 1 in 39,800 | 1 in 260,000 |
| 0.34 | 1 in 11,500 | 1 in 536,000 |
| 0.35 | 1 in 3,630 | 1 in 1.12 million |

FIG. 12

BIOMETRIC PERSONAL IDENTIFICATION SYSTEM BASED ON IRIS ANALYSIS

BACKGROUND OF THE INVENTION

This invention is related to the field of personal identification, and more specifically to the field of automated identification of humans by biometric indicia.

Identification of humans is a goal as ancient as humanity itself. As technology and services have developed in the modern world, human activities and transactions have proliferated in which rapid and reliable personal identification is required. Examples include passport control, computer login control, bank automatic teller machines and other transactions authorization, premises access control, and security systems generally. All such identification efforts share the common goals of speed, reliability, and automation.

The use of biometric indicia for identification purposes requires that a particular biometric factor be unique for each individual, that it be readily measured, and that it be invariant over time. Although many indicia have been proposed over the years, fingerprints are perhaps the most familiar example of a successful biometric identification scheme. As is well known, no two fingerprints are the same, and they do not change except through injury or surgery. It is equally clear, however, that identification through fingerprints suffers from the significant drawback of requiring physical contact with the person. No method exists for obtaining a fingerprint from a distance, nor does any such method appear likely.

A biometric indicator that has been largely ignored by the art is the iris. The iris of every human eye has a unique texture of high complexity, which proves to be essentially immutable over a person's life. No two irises are identical in texture or detail, even in the same person. As an internal organ of the eye the iris is well protected from the external environment, yet it is easily visible even from yards away as a colored disk, behind the clear protective window of the eye's cornea, surrounded by the white tissue of the eye. Although the iris stretches and contracts to adjust the size of the pupil in response to light, its detailed texture remains largely unaltered apart from stretching and shrinking. Such distortions in the texture can readily be reversed mathematically in analyzing an iris image, to extract and encode an iris signature that remains the same over a wide range of pupillary dilations. The richness, uniqueness, and immutability of iris texture, as well as its external visibility, make the iris suitable for automated and highly reliable personal identification. The registration and identification of the iris can be performed using a videocamera without any physical contact, automatically and unobtrusively.

By comparison, other biometrics such as signatures, photographs, fingerprints, voice prints, and retinal blood vessel patterns all have significant drawbacks. Although signatures and photographs are cheap and easy to obtain and store, they are impossible to identify automatically with assurance, and are easily forged. Electronically recorded voice prints are susceptible to changes in a person's voice, and they can be counterfeited. Fingerprints or hand prints require physical contact, and they also can be counterfeited and marred by artifacts.

Iris identification is not to be confused with retinal identification. The iris is easy to see and can readily be imaged with a videocamera. The retina, on the contrary, is hidden deep within the eye, and is difficult to see. Common conditions such as small pupils or cataracts make it difficult or impossible to see the retina, but they do not affect the visibility of the iris.

The only previous attempt to take advantage of these favorable characteristics of the iris for a personal identification system is seen in U.S. Pat. No. 4,641,349, issued to Flom and Safir and entitled "Iris Recognition System," (hereinafter '349). The '349 reference discloses the general concept of using the iris as a method of identification, but it does not describe a developed embodiment of such a system. It does not disclose automatic means to find and isolate the iris within an image, regardless of the location and size of the iris, nor means to extract and encode its texture. Moreover, the '349 reference does not describe any method for computing an identification decision once a list of features has been compiled. In general, a listing of features from two iris images will partially agree and partially disagree, whether or not they originated from the same iris. Generally such lists will also differ in the number of features they comprise. No theoretical or mathematical formulation was provided for basing decisions on such comparisons between incommensurate data sets. Moreover, no method was disclosed for calculating the confidence levels associated with identifications.

SUMMARY OF THE INVENTION

The broad object of the present invention is to provide a system for identifying persons based on the iris of either eye.

A further object of the invention is to provide a system for extremely reliable and rapid identification of a person, in approximately one second.

Another object of the invention is to provide an identification system that calculates confidence levels for any identification decision, on an objective and rigorous basis.

A still further object of the invention is to provide an identification system that provides identification without action from the subject and without making physical contact with the subject.

A yet further object of the invention is to provide an identification system that allows discrimination between genuine living subjects and imposters employing non-living duplicate identification means.

These and other objects are achieved in the present invention by a method for uniquely identifying a particular human being that comprises the following steps. First, the system acquires through a videocamera a digitized image of an eye of the human to be identified. Then, it isolates the iris if it is present within the image and defines a circular pupillary boundary between the iris and pupil portions of the image, and it defines another circular boundary between the iris and sclera portions of the image, using arcs that are not necessarily concentric with the pupillary boundary. The system of the invention establishes a polar coordinate system on the isolated iris image, the origin of the coordinate system being the center of the circular pupillary boundary. It then defines a plurality of annular analysis bands within the iris image, these analysis bands excluding certain preselected portions of the iris image likely to be occluded by the eyelids, eyelashes, or specular reflection from an illuminator.

The portion of the iris image lying within these annular analysis bands is analyzed and encoded employing a special signal processing means comprising a multiscale, self-similar set of quadrature bandpass filters in polar coordinates, to generate an iris code of fixed length and having a universal format for all irises. The resulting code is stored as a reference code. Because of the universal format and length of all such iris codes, comparisons among different iris codes are extremely efficient and simple. Specifically, a comparison between any two iris codes is achieved by computing the elementary logical XOR (exclusive-OR logical operation) between all their corresponding bits, and then computing the norm of the resulting binary vector. This comparison measure can also be described as the Hamming distance between the two iris code vectors. The universal format of iris codes also lends itself to rapid parallel search across large data bases of stored reference iris codes in order to determine the identity of an individual.

To perform an identification using the reference code, the system generates from an identification subject an identification code according to the providing, defining, determining, establishing, describing and analyzing steps. Then, the system compares the identification code with the reference code, to ascertain the Hamming distance between the codes. This distance is then converted into a calculated likelihood that the two codes originated from the same iris, and hence from the same person, by computing the probability that the observed matching fraction of bits in the two codes could match by chance if the two codes were independent. A preselected criterion applied to this measured Hamming distance generates a "yes" or "no" decision, and the confidence level for the decision is provided by the calculated probability.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

FIG. 12 is a table of performance rates achieved with the present invention.

DETAILED DESCRIPTION OF THE PREFERRED EMBODIMENT

Figure 1:
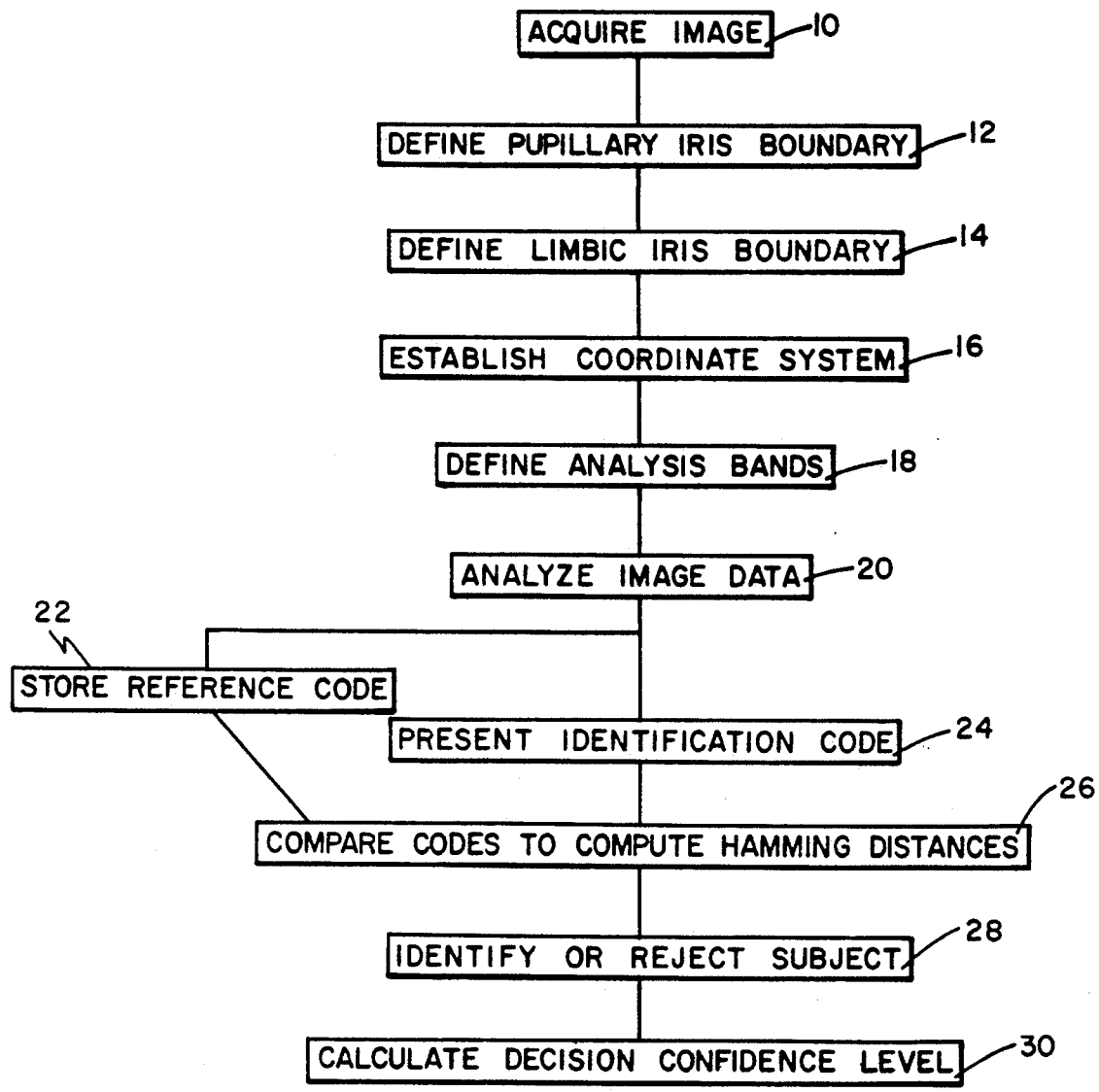
FIG. 1 is a block diagram depicting the principal steps of the process of the present invention.

An embodiment of the present invention is shown in schematic form in FIG. 1 and comprises a block diagram depicting the principal steps in developing an iris identification code for a person, and then using that code to make an identification. The process will be discussed in overall terms, followed by a detailed analysis.

The iris of the human eye is a complex structure comprising muscle, connective tissue, blood vessels, and chromatophores. Externally it presents a visible texture with both radial and angular variation arising from contraction furrows, collagenous fibers, filaments, serpentine vasculature, rings, crypts, and freckles; taken altogether, these constitute a distinctive "fingerprint." The magnified optical image of a human iris, thus constitutes a plausible biometric signature for establishing or confirming personal identity. Further properties of the iris that lend themselves to this purpose, and render it potentially superior to fingerprints for automatic identification systems, include the impossibility of surgically modifying its texture without unacceptable risk; its inherent protection and isolation from the physical environment; and its easily monitored physiological response to light. Additional technical advantages over fingerprints for automatic recognition systems include the ease of registering the iris optically without physical contact, and the intrinsic polar geometry of the iris, which imparts a natural coordinate system and origin.

Unknown until the research leading to the present invention was whether there are sufficient degrees-of-freedom, or variation in the iris across individuals, to impart to it the same singularity as a conventional fingerprint. Also uncertain was whether efficient algorithms could be developed to extract detailed iris structure reliably from a video image, generate a compact code (of miniscule length compared with image data size), and render a decision about identity with high statistical confidence, all within a few seconds of processing time on conventional equipment. The present invention resolves all of these questions affirmatively.

At the broadest level, the system of the present invention can be envisioned in five steps. First, an image of the eye to be analyzed must be acquired in digital form suitable for analysis, as shown in block 10 of FIG. 1. Then, the iris portion of the image must be defined and isolated (blocks 12, 14, 16 and 18). The defined area of the image must next be analyzed to produce an iris code (block 20). It should be noted that the first iris code generated for a particular iris is stored as a reference code (block 22). In subsequent encounters, the system uses the reference code to make an identification by comparing a presented code (block 24) with the reference code to obtain a Hamming distance (block 26). This data permits the system to establish, confirm, or disconfirm the identity of the subject (block 28), and to calculate a confidence level for the decision (block 30).

Figure 2:
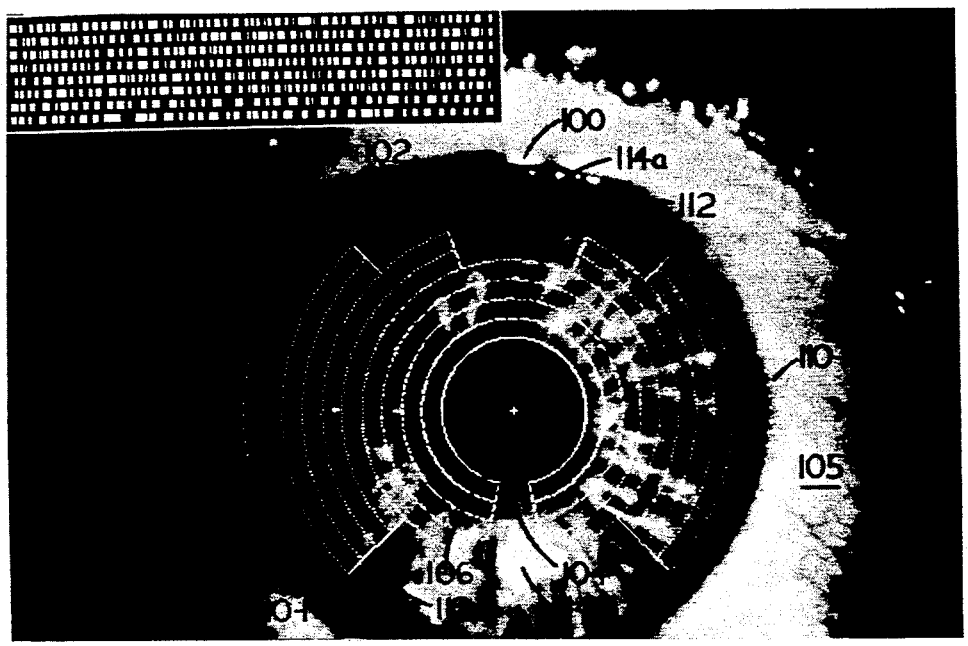
FIG. 2 is a photograph of a human eye, overlaid to demonstrate the process of the present invention.

In a practical application of this system, a digitized image as illustrated in FIG. 2 shows an eye 100 with an iris 102 surrounding a pupil 104. The eye's sclera portion 105 which is the white portion in turn surrounds the iris 102. The first step in processing the image is to locate the pupillary boundary 106, separating the pupil 104 from the iris 102, to a high degree of accuracy (block 12, FIG. 1). This step is critical to insure that identical portions of the iris are assigned identical coordinates every time an image is analyzed, regardless of the degree of pupillary dilation.

The inner boundary of the iris, forming the pupil, can be accurately determined by exploiting the fact that the boundary of the pupil is essentially a circular edge. As seen in FIG. 2, the pupil 104 is generally dark while the iris 102 is lighter, with varied pigmentation. However, this relationship may sometimes be reversed, for example in eyes with dark irises and some cloudiness of the internal lens, or because of optically co-axial illumination (directly into the eye), in which case light is reflected back from the retina and out again through the pupil. A further reason that the image of the pupil may be bright is because of specular reflections from the cornea. A general purpose method for finding the pupillary boundary should be robust enough to function reliably whether or not the region of the pupil is actually darker than the iris. In the present invention, a system of integrating evidence about the true pupillary boundary has been developed which has the desired robust behavior and accuracy.

The method of the present invention detects the pupillary boundary as an abrupt and sudden change in brightness when summed along a circle whose radius is steadily increasing. This sudden change will be maximum if the circle has its center near the true center of the pupil, and when its radius matches the true radius of the pupil. Thus, the image processing problem of finding the pupil can be formulated as an optimization problem, in which a series of "exploding circles" (steadily increasing radii) are positioned with their center coordinates located at each one of a number of trial points on a grid. For each exploding circle, and for each value of its radius, the total image brightness is summed over a fixed number of points lying on this circle. (Using a constant number of points on each circle, typically 128, avoids an automatic increase in the summed brightness simply due to increasing circumference.) The system searches for the maximum rate of change in this quantity as radius expands. For the candidate circle that best describes the pupillary boundary, there will be a sudden "spike" in the rate-of-change of luminance summed around its perimeter, when its radius just matches that of the pupillary boundary. This spike will be larger for a circle that shares the pupil's center coordinates and radius, than for all other circles. In this manner, the problem of precisely locating the pupil has been converted into an optimization problem in which a three-parameter space is searched for the best combination of circle center coordinate $(x_0, y_0)$ and radius r.

The process of the instant invention can be described mathematically as summing a contour integral of image intensity, $I(x,Y)$, over the arc (ds) of a circle whose radius is r and whose center coordinates are $(x_0, y_0)$; and then computing the partial derivative of this quantity with respect to r as the radius increases. The maximum absolute value of this derivative is sought, over the space of the three parameters $(x_0, y_0, r)$:

$$\max_{(r, x_0, y_0)} \left| \left| \frac{\partial}{\partial r} \phi_{r, x_0, y_0} I(x, y) ds \right| \right| \quad (1)$$

The partial derivative with respect to r can be a smoothed, or blurred, derivative for noise immunity, and it may also be converted into a percentage change (dividing by the current value of the contour integral) for enhanced noise immunity. The method also has some intrinsic noise immunity, because the contour integral inherently integrates data over a contour, so any anomalous excursions in pixel brightness tend to average out.

The search process in the three-parameter space is directed by gradient ascent, or "hill-climbing." If a candidate series of exploding circles is partially within the pupil, the value of the quantity defined in Equation (1) will be larger than for other circles. The closer the center of the concentric circles comes to the true pupillary center, the larger will be this quantity. Similarly, the quantity within Equation (1) will be larger for circles of appropriate radius. Thus, the method can find the optimal combination of the three parameters by an iterative search process, in which the stepsize of changes in the three parameters is decreasing with each successive iteration. By moving always in the best direction (in which the rate of improvement is greatest) in the three-parameter space, and by taking stepsizes proportional to the rate of improvement, and by decreasing these stepsizes on each successive iteration, the method rapidly converges. After usually only four or five iterations, the optimal values of the three parameters have been determined to within less than one pixel. The values for $(x_0, y_0, r)$ determine the estimate pupillary boundary, as well as the origin of the polar coordinate system for subsequent iris analysis.

This efficient method of finding and tracking the pupillary boundary also provides an important safeguard against imposters. One obvious method for trying to defeat an identification system based on iris patterns would be to present to the videocamera a photograph of anothers person's eye, or even to wear contact lenses imprinted with the image of an authorized iris. However, an important feature of a living eye is that the pupil diameter undergoes small oscillations ("hippus") once or twice per second, even under uniform lighting. A photograph of an iris, or a contact lens imprinted with an iris image, would not exhibit such variation in time. Because the process described above for finding and tracking the pupillary boundary is so rapid, it is possible to acquire several images in succession and to monitor the pupillary diameter over time. An absence of hippus oscillations or other small variations in iris pattern over time would constitute evidence that a photograph or simulacrum were being presented, rather than a living iris, and this would indicate an intrusion attempt. This ability to discriminate between a living iris and a simulacrum or photograph is an important security asset, made possible by the rapid means for defining and tracking the pupillary boundary.

Once the boundary and center have been determined, the next step is to locate the outer boundary of the iris, or limbus, where it meets the sclera. An important consideration here is the fact that the pupil is not always centered within the iris. The radial distances to the right and left limbus may vary by as much as 20%, and hence both distances must be computed in order to generate an appropriate iris coordinate system. A further consideration is the fact that the upper and lower eyelids generally obscure the top and bottom boundaries of the iris, and hence these regions should be excluded from iris analysis.

The same general method of "exploding circles" that yielded accurate determination of the pupillary boundary can be used for finding the outer boundary of the iris, but with two modifications. First, given the upper and lower eyelid occlusions and the generally unequal left and right limbic distances, the method is restricted to just two arcs along the horizontal meridian, one at 3-o'clock and one at 9-o'clock, each subtending $\pi/4$ radians (45 degrees). The distances to these two boundaries on either side of the iris are measured separately. Second, because of possible concentric texture within the iris that could produce a maximum in Equation (1), the contour integral used earlier for the pupillary boundary is replaced by an area integral that blurs outs iris detail in searching for the limbus. In effect, the "exploding circles" are replaced by two horizontally "exploding pie wedges," that search for a sustained luminance step signifying the sclera on either side. As before, the search process remains one of finding the maximum in the rate-of-change of integrated luminance as the radius of expansion increases. After compensation for the increasing area of luminance integration, the maximum in this derivative with respect to radius invariably corresponds to the correct left and right boundaries of the iris.

Mathematically, this operation is implemented by searching for the value of r (the distance from the pupillary center to either the right or the left) which maximizes the expression $$\max_{r \in [1.5r_0, 10r_0]} \frac{\partial}{\partial r} \int_{\rho=r-\delta}^{r+\delta} \frac{2}{\pi\delta r} \int_{\theta=\phi-\pi/8}^{\phi+\pi/8} I(\rho,\theta)\rho d\rho d\theta \quad (2)$$

where $r_0$ is the pupillary radius (computed earlier), $\delta$ is a thin radial shell (typically 0.1 $r_0$), I ($\rho$, $\theta$) is the image intensity, now expressed in terms of polar coordinates $\rho$ and $\theta$, and $\phi$ equals either 0 or $\pi$, corresponding to either the 3-o'clock or the 9-o'clock meridian, respectively. It has been found successful to compute this expression for values of r between 1.5 $r_0$ and 10 $r_0$ (i.e., 1.5 times to 10 times the pupillary radius) in searching for the outer boundaries of the iris, thus covering a wide range of possible relative diameters of pupil and iris. Similarly, the choice of $+/-\pi/8$ radians as the arc angle of integration in Equation (2) has proven a useful horizontal angular delimiter for the pie wedges, to avoid the upper and lower eyelids. The calculated results from Equation (2) are shown in FIG. 2 as the series of white dots, 110-*l* and 110-*r* on the iris 102, which correctly correspond to the left and right boundaries of the iris.

In summary Equation (1) finds the inner boundary of the iris, i.e., the pupillary boundary. This equation generates a series of "exploding circles" at various center positions, searching iteratively for the one combination of parameters ($x_0$ and $y_0$ center, and radius r) at which the integrated luminance along the circle undergoes the greatest absolute value of rate-of-change. Hence, we seek the maximum absolute value of the partial derivative with respect to r, of the contour integral of luminance along the circle. This search covers the $x_0$, $y_0$, r parameter-space, in a very efficient iterative process of gradient-ascent. Equation (2) finds the outer boundary of the iris, namely the limbus, where the white sclera begins. The same process of exploding circles as in Equation (1) would work, but for (i) upper and lower eyelid occlusion which could cause difficulties; and (ii) the fact that the iris is less uniform than the pupil, and may have large "circular edges" itself that could trap the algorithm of Equation (1). So Equation (2) instead specifies a series of "exploding pie wedges" in the horizontal meridian (hence avoiding upper and lower eyelids), and integrates luminance within pie wedges rather than just along a circle. Therefore, Equation (2) specifies an area integral in polar coordinates that is differentiated with respect to radius, rather than a contour integral as in Equation (1).

With the locations of the pupillary boundary and the limbus established, and the origin of polar coordinates fixed at the center of the pupil, a series of zones of analysis are assigned to regions of the iris. These are defined concentrically at fixed linear fractions of the radial distance between pupil and limbus, whatever may be the overall size of the iris in a given image, to achieve size invariance in the code. Thus the polar coordinate system for the iris is dimensionless in both its angular and radial coordinates. Since the iris can be approximately modelled as a rubber sheet that stretches and contracts with the pupillary reflex, its texture and markings stretch and shrink accordingly. These distortions are eliminated by the use of a radial coordinate that marks off distance simply as different fractions of the total distance from the inner boundary of the iris (the pupil) to its outer boundary. Thus a given iris, in different states of pupillary dilation on different occasions, should generate approximately the same iris code. A second purpose served by this dimensionless coordinate system is that differences in the overall size of the iris image per se, due to image acquisition from different distances, will not change the computed iris code.

Since the pupil in general is not perfectly centered horizontally within the iris, it is necessary for the fractionation to be based on a linear combination of right and left limbus estimates, weighted cosinusoidally by angle. Due to frequent partial occlusion of the upper iris by the upper eyelid, and specular reflection from the cornea obscuring part of the lower iris, these areas are excluded from analysis and encoding. An illustration of these ultimate zones of analysis, superimposed upon a particular iris image, may be seen in FIG. 2.

Specifically, the portion of the iris to be analyzed is mapped and subdivided into analysis bands 112 (see FIG. 2). These analysis bands are defined in a special polar coordinate system whose radial coordinate may be slightly distorted if, as frequently occurs, the inner and outer boundaries of a particular iris are not concentric. Specifically, for any angular coordinate around the iris, the radial coordinate r of some point is defined by its fraction of the distance from the pupillary boundary to the sclera, along that ray. Thus, just as an angular coordinate is (classically) a dimensionless quantity between 0 degrees and 360 degrees, so also the radial coordinate is dimensionless in this bounded system, lying always in the interval between 0 and 1, regardless of the overall size of the iris image and regardless of the degree of pupillary dilation. Hence this doubly-dimensionless polar coordinate system is inherently size-invariant (thus inherently compensating for variation in the distance from the eye to the videocamera). Similarly, the coordinate system also inherently compensates for any non-concentricity of the inner and outer boundaries of an iris.

Four additional special features of the analysis bands 112 are needed to compensate for the departure of many iris images from the ideal, annular stereotype. First, since the pupil 104 itself often has an irregular boundary, the innermost analysis band starts with a radius of about 1.1 times the pupil's average radius in order to ensure exclusion of the pupil entirely. Similarly, since the transition from iris 102 to sclera 105 may likewise be irregular and non-circular, the outermost analysis band extends radially only to about 80% of the distance to the outer boundary of the iris (as measured to the right and left, with cosinusoidal weighing in intermediate angles). Third, provision must be made for the occlusion of the upper and lower portions of the iris by the eyelids, and fourth, for a specular reflection that may cover part of the iris if an oblique source of illumination is used (typically from below). These spurious features are excluded by restricting the outermost analysis bands to two cones around the horizontal meridian, thus avoiding the regions likely to be occluded by the upper and lower eyelids and by also excluding a narrow notch around the 6-o'clock position for the specular reflection of illumination below. These excluded areas are noted in FIG. 2 as 114$a$ and 114$b$. It is preferred to divide the iris area into as many as eight annular bands 112 for analysis, at fixed radial fractions of the distance between the inner and outer boundaries as defined above.

Having accurately defined the image area subject to analysis, the system then processes the data obtained from that area to generate the identification code, as depicted in block 20 of FIG. 1. Unlike the system described in the prior art, the present invention does not depend on controlling the amount of pupillary dilation. Rather, because of the dimensionless radial coordinate that simply measures off certain fractions of the distance from the inner boundary to the outer boundary of the iris, any given piece of iris tissue will always fall into the same zone of analysis, with the same position coordinates, regardless of how stretched or compressed the iris happens to be due to pupillary dilation. This dimensionless coordinate system exploits the fact that the stretching of the iris can be approximated as the stretching of a rubber sheet, so that its markings can still be recovered mathematically in undistorted form because the coordinate system is stretched an equal amount. Therefore, the texture of the iris is always encoded into essentially the same iris code, regardless of the degree of pupillary dilation, and regardless also of the overall size of the iris image.

An effective strategy for extracting textural information from images, such as the detailed patterns of the iris, is convolution with quadrature bandpass filters such as 2-D Gabor filters. These 2-D filters were proposed by the inventor in 1980 and 1985 both as a framework for understanding orientation- and frequency-selective receptive field properties observed in neurons in the primate visual cortex, and as useful operators for practical image analysis problems. See Daugman, J. (1980) "Two-Dimensional Spectral Analysis Of Cortical Receptive Field Profiles," *Vision Research* 20, pp. 847–856; and Daugman, J. (1985) "Uncertainty Relation For Resolution In Space, Spatial Frequency, And Orientation Optimized By Two-Dimensional Visual Cortical Filters," *Journal Of The Optical Society Of America*, Volume 2 (7), pp. 1160–1169. As conjointly optimal filters they offer maximum resolution simultaneously for spatial frequency and orientation information, together with 2-D position; they uniquely achieve the lower bound for joint uncertainty over these four variables, as dictated by an inescapable uncertainty principle. These properties are particularly useful for texture analysis, because of the 2-D spectral specificity as well as positional dependency of texture.

Figure 3A:
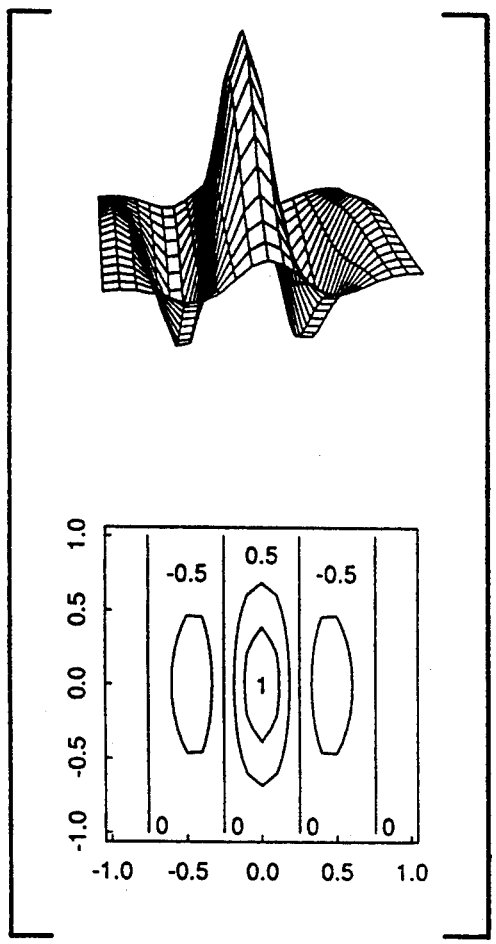
FIGS. 3a and b illustrates the quadrature bandpass filters employed by the present invention as image convolution kernels to extract iris structure at many scales of analysis.
Figure 3B:
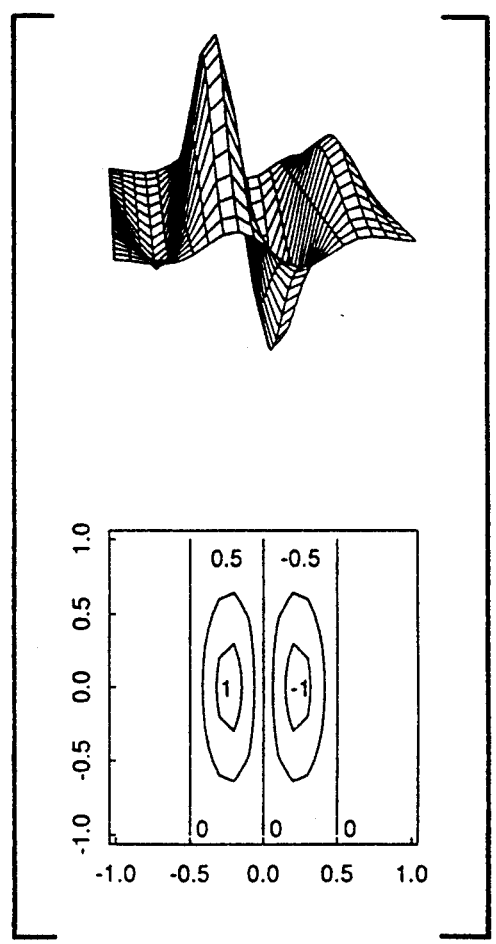

Two members of the family of 2-D Gabor filters are illustrated in FIG. 3, as even-symmetric and odd-symmetric wavelet profiles together with their contour plots. These localized, undulating 2-D functions, defined at many different sizes and positions, are multiplied by the raw image pixel data and integrated over their domain of support to generate coefficients which describe, extract, and encode image texture information. Applicant has given these the name "2-D Gabor filters," because they are a 2-D generalization of a class of elementary functions discussed in one dimension in 1946 by Dennis Gabor. See Gabor, D. (1946) "Theory Of Communication," *J. Ins. Elec. Eng.*, Vol. 93, pp. 429–457.

The 2-D Gabor filters used in the present invention are defined in polar coordinates as follows:

$$G(r,\theta) = e^{-2\pi i \omega (\theta - \theta_0)} e^{-(r-r_0)^2/\alpha^2} e^{-(\theta - \theta_0)^2/\beta^2} \quad (3)$$

where r is radius, $\theta$ is angular distance in radians, $\omega$ is frequency, and $\alpha$ and $\beta$ are constants.

Both the real and imaginary members of the quadrature (even-and odd-symmetric) pair of filters projected from the above analytic function are used. Free parameters $\alpha$ and $\beta$ co-vary in inverse proportion to $\omega$ to generate a multi-scale self-similar family of frequency-selective quadrature filters. They are in quadrature because both orthogonal phases are used at each position. They are self-similar because the inverse proportionality of their size and frequency parameters renders them all dilates of each other, sharing a common shape. Their locations, specified by $\theta_0$ and $r_0$, range across the zones of analysis of the iris.

Figure 4A:
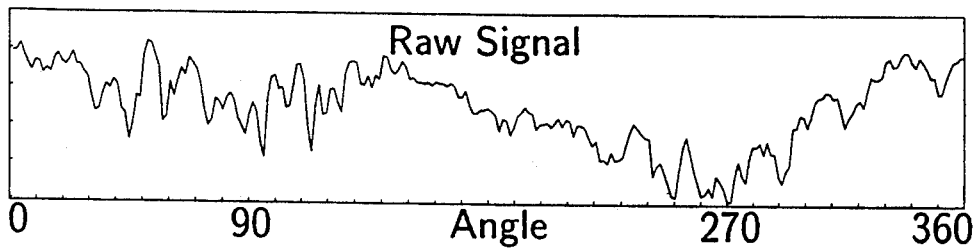
FIGS. 4A-4C are a set of plots illustrating how iris image data is converted into iris code bits by the quadrature bandpass filters according to the present invention.
Figure 4B:
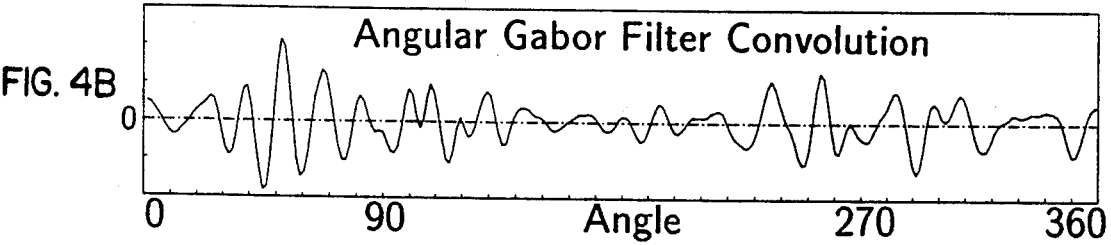
Figure 4C:
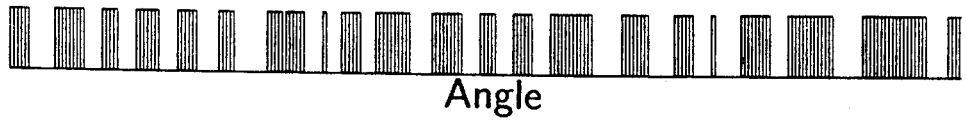

The manner in which an iris code is generated by passing 2-D Gabor filters over the iris, in polar coordinates, is illustrated in FIGS. 4A, 4B and 4C. The upper trace (FIG. 4A) shows a 1-D scan around the iris at a particular radius, and plots the luminance of the image as a function of the angular coordinate around the iris. (For simplicity, the image is represented here as just a 1-D signal rather than a 2-D signal.) The second trace (FIG. 4B) shows the response of a Gabor filter with a particular size and symmetry, positioned over each corresponding angular coordinate of the iris. It should be noted that because of the bandpass character of Gabor filters, their response to the raw input signal can be either positive or negative, and is centered around zero. The slow, non-informative modulation in the luminance of the raw signal, up and down around the iris resulting from the illumination from below, is removed by the bandpass Gabor filters, as is the high frequency noise.

Each bit in an iris code is determined by whether the response of a particular 2-D Gabor filter, having a certain size, symmetry, and position over the iris, is positive or negative. This process is denoted in Equations 4, 5, 6 and 7. Because it is a "sign bit" that is encoded, this information corresponds to the Most Significant Bit (MSB) of the coefficient that results from integrating the product of a 2-D Gabor filter with the input image, as described earlier. The use of both even and odd quadrature symmetries of 2-D Gabor filters, extracting independent information, is denoted by the subscripts Re and Im for the bits determined by the corresponding Real and Imaginary parts of the 2-D Gabor filters in complex form:

$$MSB_{Re}(r,\theta) = 1 \text{ if}$$
$$Re \int_\rho \int_\phi e^{-2\pi i\omega(\theta-\phi)} e^{-(r-\rho)^2/\alpha^2} e^{-(\theta-\phi)^2/\beta^2} I(-\rho,\phi) \rho d\rho d\phi > 0 \quad (4)$$

$$MSB_{Re}(r,\theta) = 0 \text{ if}$$
$$Re \int_\rho \int_\phi e^{-2\pi i\omega(\theta-\phi)} e^{-(r-\rho)^2/\alpha^2} e^{-(\theta-\phi)^2/\beta^2} I(-\rho,\phi) \rho d\rho d\phi \leq 0 \quad (5)$$

$$MSB_{Re}(r,\theta) = 1 \text{ if}$$
$$Re \int_\rho \int_\phi e^{-2\pi i\omega(\theta-\phi)} e^{-(r-\rho)^2/\alpha^2} e^{-(\theta-\phi)^2/\beta^2} I(-\rho,\phi) \rho d\rho d\phi > 0 \quad (6)$$

$$MSB_{Re}(r,\theta) = 0 \text{ if}$$
$$Re \int_\rho \int_\phi e^{-2\pi i\omega(\theta-\phi)} e^{-(r-\rho)^2/\alpha^2} e^{-(\theta-\phi)^2/\beta^2} I(-\rho,\phi) \rho d\rho d\phi \leq 0 \quad (7)$$

These conditionals (Equations 4–7) determine each of the 2,048 bits in an iris code, across multiple scales of analysis (set by parameters $\alpha$, $\beta$ and 107) and across all of the sampled positions (set by polar coordinate parameters r and $\theta$) within the defined zones of analysis of the iris image. It is noteworthy that a very significant amount of data compression is achieved in such a code because of its decorrelating nature. Whereas the original iris image may consist of typically 262,000 bytes (a 512×512 array of pixels, each pixel requiring one byte), the significant iris texture has been reduced by this multi-scale 2-D Gabor code to a very compact signature comprising only 1/1,000th as much data (namely 256 bytes).

An example of a 256-byte iris code is inscribed at the top of FIG. 2, organized as 256 angular columns, each with 8 bits computed over the concentric zones of analysis. Although there are 2,048 bits in any given code, a code possesses fewer than 2,048 independent binary degrees-of-freedom. The chief reason is that there exist substantial radial correlations in an iris. For example, a given furrow tends to propagate across a significant radial distance, and thus it exerts its influence on several remote parts of the code. A second reason is that correlations are introduced by the low-pass property of the 2-D Gabor filters. Specifically, any signal convolved with a linear filter acquires a correlation distance equal to the reciprocal of the bandwidth of the filter.

Figure 5:
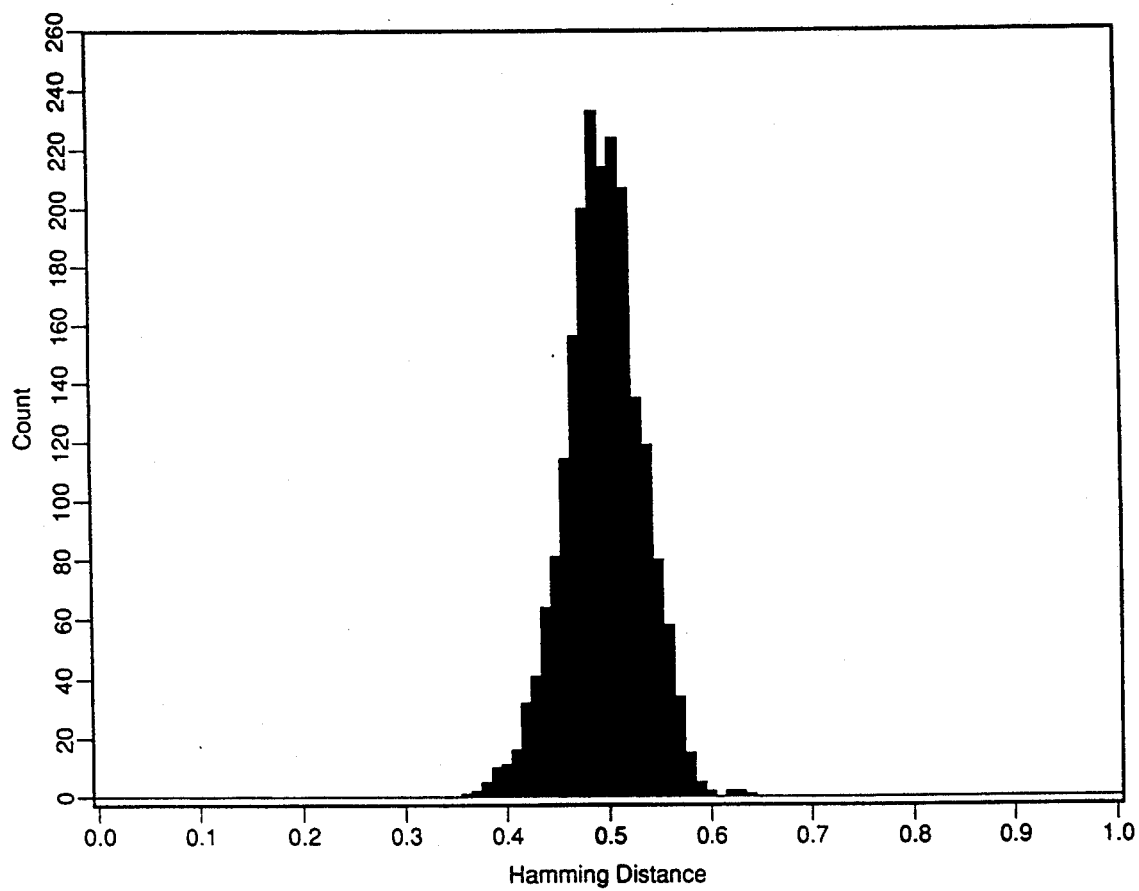
FIG. 5 is a plot showing the Hamming distances for "imposters", i.e., for comparisons between iris codes computed from different irises.
Figure 10:
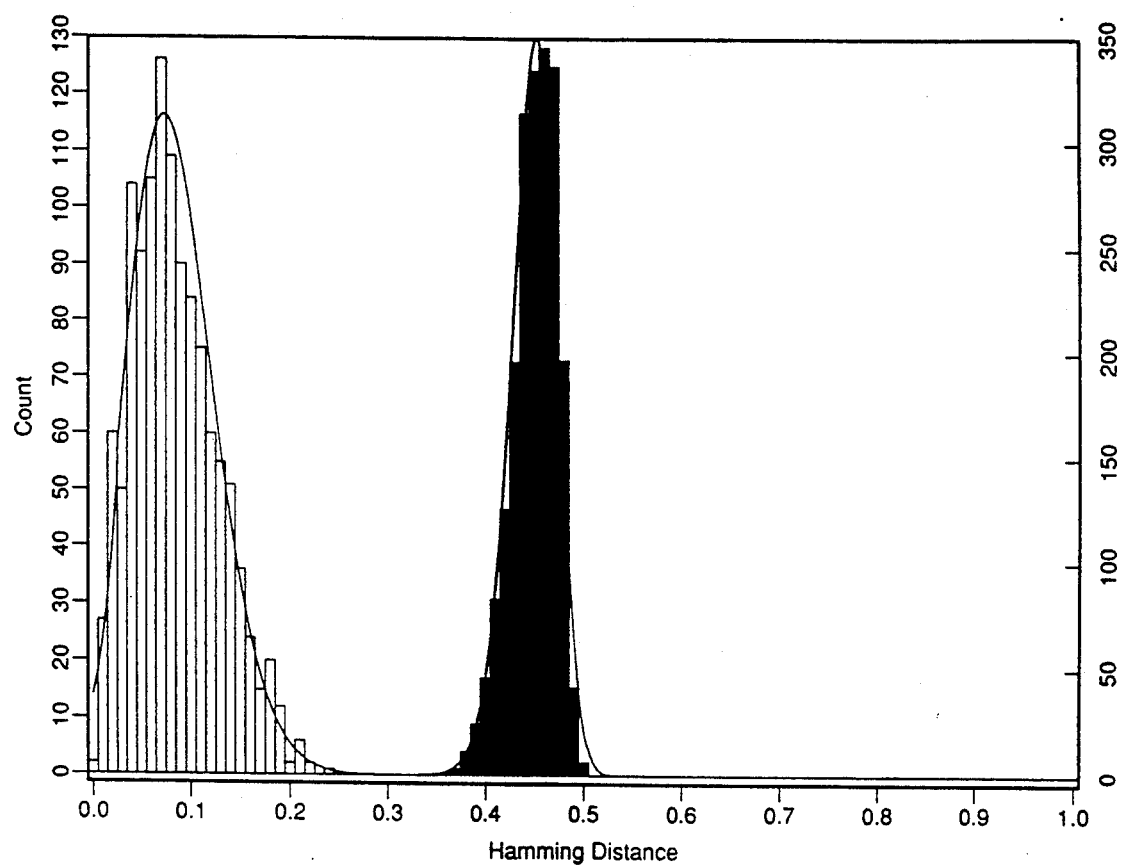
FIG. 10 is a plot showing binomial fit to Hamming distance distributions.

The actual number of independent degrees-of-freedom can be estimated by examining the distribution of Hamming distances (fraction of disagreeing bits) across a large population of iris codes, comparing each code bit-by-bit with every other code computed from a different iris. Since each bit has equal probability of being a 1 or a 0, there is a probability p=0.5 that any pair of bits from different iris codes disagree. If each of the 2,048 bits in a given code were independent from every other bit, then the distribution of observed Hamming distances should be equivalent to a binomial distribution with p=0.5 and N=2,048 (in other words, equivalent to tossing a fair coin repeatedly and counting the fraction of heads in each round of 2,048 tosses). The actual distribution of observed Hamming distances among codes from different irises is shown in FIG. 5. Its standard deviation is $\sigma=0.038$, around a mean of $\mu=0.497$. Since the standard deviation of a binomial distribution is given by $$\sigma = \sqrt{pq/N},$$

the observed distribution of Hamming distances is equivalent to a binomial distribution with N=173 bits; an actual fit of such a binomial to the observed iris code data, which may be seen in FIG. 10, reveals an excellent match. Thus there are approximately 173 independent binary degrees-of-freedom in a 2,048-bit iris code. This estimate is corroborated by a second estimate, obtained by applying the Lempel-Ziv compression algorithm to the iris codes. This procedure generates decorrelated iris codes having an average length of 194 bits (roughly 24 bytes).

Using the binomial estimate of N=173 binary degrees-of-freedom as a measure of the complexity or dimensionality of a 2,048-bit iris code, we can compute the likelihood of two codes from different irises matching by chance. Since the 2-D Gabor filters have no positive or negative bias, the a priori odds of any given bit being a 1 or a 0 are even, and hence the probability is 0.5 that two corresponding bits in two different iris codes would be the same. Factoring in the partial correlations within an iris code but assuming independence between iris codes, the odds that two different irises might generate the same code are one in $2^{173}$, which equals one in $10^{52}$.

The process of comparing any two iris codes (FIG. 1, Block 26), such as a previously stored one (Block 22) and one that is currently computed from a presenting image (Blocks 24), is very simple because of the universal format and fixed length of all such codes. A similarity metric called a Hamming distance is computed, that measures "distance," or similarity between the two codes. This measure simply adds up the total number of times that two corresponding bits in the two iris codes disagree. Expressed as a fraction between 0 and 1, the Hamming distance between any iris code and an exact copy of itself would therefore be 0, since all 2,048 corresponding pairs of bits would agree. The Hamming distance between any iris code and its complement (in which every bit is just reversed), would be 1. The Hamming distance between two random and independent strings of bits would be expected to be 0.5, since any pair of corresponding bits has a 50% likelihood of agreeing and a 50% likelihood of disagreeing. Thus, if two iris codes arise from different eyes, their Hamming distance would be expected to be 0.5; if they arise from the same eye, on different occasions, their Hamming distance would be expected to be considerably lower. If both iris codes were computed from an identical photograph, their Hamming distance should approach zero.

Comparisons between iris codes can be made with several different relative shifts along their angular axis, in order to compensate for possible tilt of the head of the subject or torsional eye rotation. These relative shifts in the code comparison process are readily implemented by lateral scrolling of the iris codes relative to each other, as though the code portrayed in the upper left corner of FIG. 2 were wrapped around into a cylinder, joining the left and right margins, and then rotating the cylinder and repeating the comparison process.

The computation of Hamming distances between iris codes is made very simple through the use of the elementary logical operator XOR (Exclusive-OR). A pair of bits A and B can have exactly four possible combinations: (AB)=(00), (01), (10), and (11). The XOR operator on two inputs is defined as 1 if one and only one of the inputs equals 1; otherwise their XOR is 0. Thus, in the example given for the four possible combinations of the bits A and B, the corresponding values of their XOR are: (A XOR B)=0, 1, 1, 0. Clearly, XOR can thus be used to detect a disagreement between any pair of bits, whatever their values.

Tallying up their total number of times that the XOR of two corresponding iris code bits equals 1, and dividing by the total number of such comparisons (which is the number of bits in an iris code), is equivalent to measuring the Hamming distance between the two codes. Alternatively, this quantity may also be described as the normalized squared length, or squared-norm, of the difference vector between the two iris code vectors in a 2,048-dimensional binary space. All of these formulations generate the same metric for iris code comparisons, and they lend themselves to immediate conversion into a computed probability that two iris codes came from the same iris, and hence from the same person.

The problem of recognizing the signature of a given iris as belonging to a particular individual, or deciding that s/he is an imposter, can be formulated within the framework of statistical pattern recognition and decision theory.

Yes/No decisions in pattern recognition have four possible outcomes: either a given pattern is or is not a true instance of the category in question; and for either of these two cases, the decision made can be correct or incorrect. These four outcomes are usually termed Hit, Miss, False Alarm, and Correct Rejection. In the present application the four possible outcomes are Acceptance of Authentic (AA), Acceptance of Imposter (IA), Rejection of Authentic (AR), and Rejection of Imposter (IR). The goal of the decision-making algorithm is to maximize the likelihoods of AA and IR, while minimizing the likelihoods of IA and AR. The pairwise trade-offs among the probabilities of these four outcomes can be manipulated in a way that reflects their associated costs and benefits in a particular application.

Figure 6:
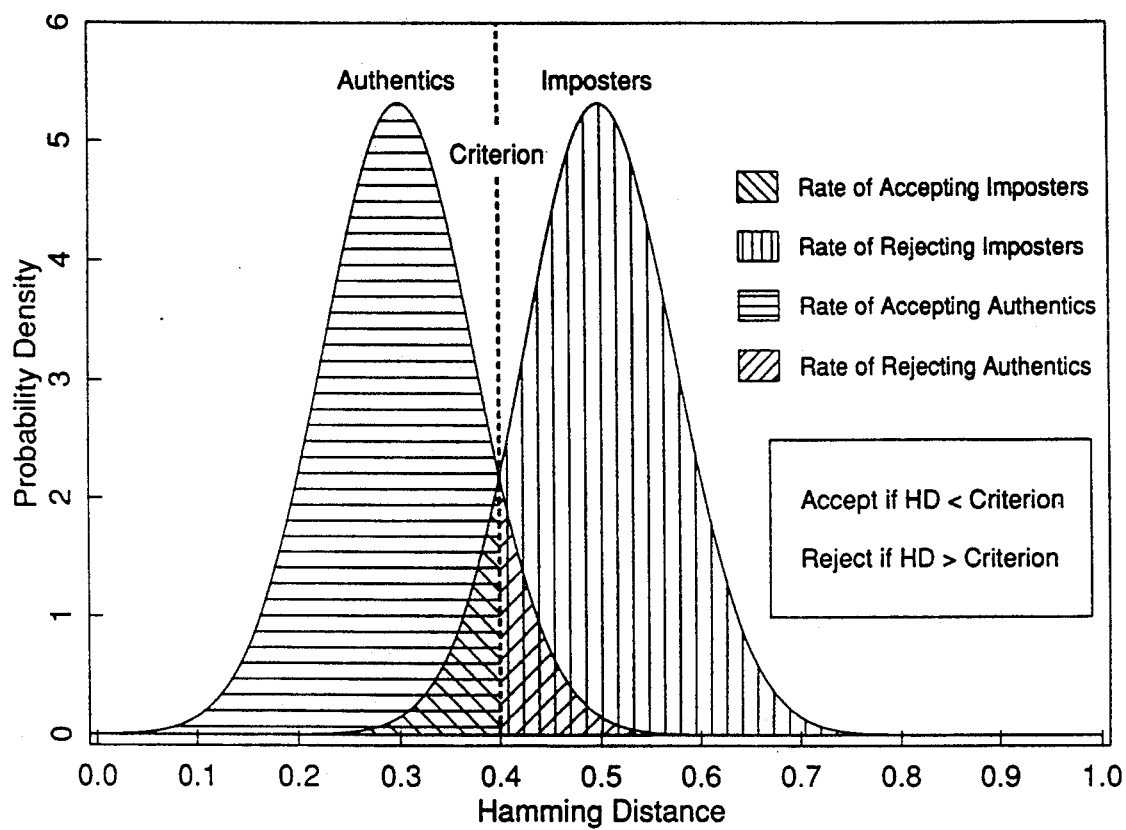
FIG. 6 is a plot showing formulation for statistical decision theory.

A formulation for decision-under-uncertainty is presented in FIG. 6. A given measurement of the Hamming distance, or fraction of disagreeing bits between two iris codes, constitutes a point on the abscissa. The measurement is regarded as being a random variable describing one of two processes, represented by the two overlapping probability distributions. It is unknown a priori which of these two distributions the random variable describes; the goal is to decide which. A criterion is chosen, as indicated by the dotted vertical line in FIG. 6, and all Hamming distances smaller than this criterion are judged to belong to the "Authentics" distribution, while all Hamming distances greater than this criterion are judged to belong to the "Imposters" distribution. These two distributions, $P_{Au}(H)$ and $P_{Imp}(H)$, give the probability density of a particular measured Hamming distance, H, arising from two comparisons of the same iris (an "authentic"), or from two comparisons of different irises (an "imposter"), respectively.

The four outcomes AA, IA, AR, and IR have probabilities that are now fully determined by the chosen criterion and by the statistical parameters of the two underlying distributions. If the decision rule is:

Accept If Hamming Distance < Criterion
Reject If Hamming Distance > Criterion then the probabilities of the four possible outcomes are equal to the areas under the two probability density functions, $P_{Au}(H)$ and $P_{Imp}(H)$, on either side of the chosen criterion, C:

$$P(AA) = \int_0^C P_{Au}(H)dH \quad (8)$$

$$P(AR) = \int_C^1 P_{Au}(H)dH \quad (9)$$

$$P(IA) = \int_0^C P_{Imp}(H)dH \quad (10)$$

$$P(IR) = \int_C^1 P_{Imp}(H)dH \quad (11)$$

These four probabilities are signified by the four shaded areas in FIG. 6.

It is clear that the four probabilities separate into two pairs which must sum to unity, and two pairs which are governed by inequalities:

$$P(AA)+P(AR)=1 \quad (12)$$

$$P(IA)+P(IR)=1 \quad (13)$$

$$P(AA)>P(IA) \quad (14)$$

$$P(IR)>P(AR) \quad (15)$$

It is also clear that the two error rates, P(AR) and P(IA), will be minimized if the two Hamming distance distributions, $P_{Au}(H)$ and $P_{Imp}(H)$, have minimal overlap. This can be achieved either by pushing their two means farther apart, or by reducing their variances, or both. It should be noted that the two distributions in general will not have the same form and variance, as was implied in FIG. 6 for simplicity.

The usefulness, or Identification Power, of a biometric signature method for distinguishing among and recognizing individuals can be defined in terms of the amount of overlap between these two distributions. Clearly, if there were no overlap, it would be possible to make correct decisions 100% of the time. Conversely, the more overlap, the higher would be the proportion of errors, regardless of the decision criterion employed.

Specifying the decision criterion C in Equations (8)–(11) above provides the ability to elect different decision strategies most suitable for different applications. For example, in controlling access to bank Automatic Teller Machines, allowing the ARR to be much higher than 0 may be bad for customer relations, even if it means tolerating a higher IAR; after all, the cost of accepting an imposter is at worst the ATM cash withdrawal limit. On the other hand, in military or embassy security systems, a far more conservative criterion is demanded, perhaps as stringent as only one chance in a million for an imposter to be admitted, even though such a criterion in this case would require tolerating a higher ARR (percentage of authentics rejected for further screening).

Figure 7:
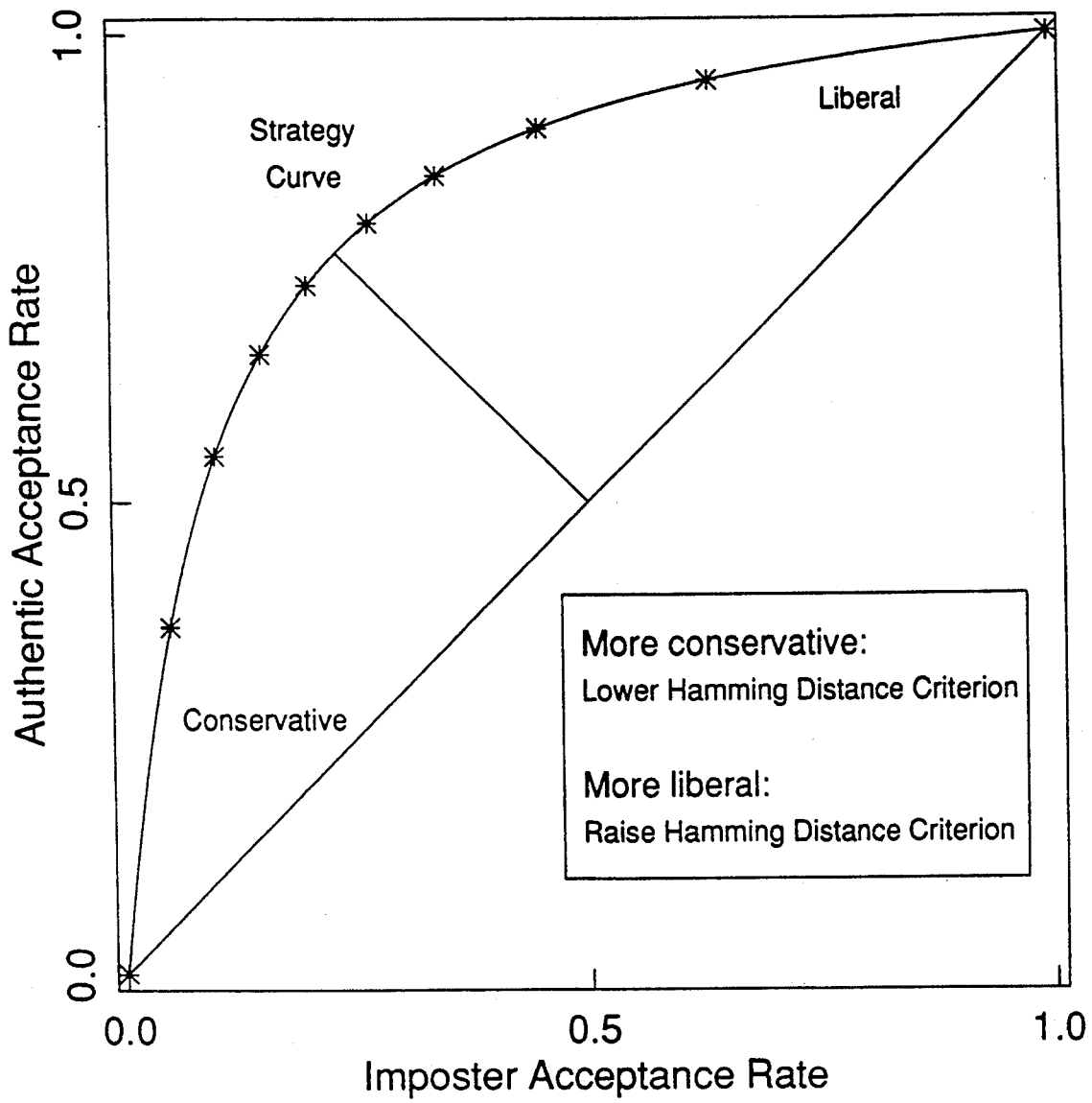
FIG. 7 is a plot illustrating the effects of manipulation of decision criterion.

The manipulation of the decision criterion C, in order to implement different decision strategies, is illustrated schematically in FIG. 7. The Authentic Acceptance Rate, or P(AA), is plotted against the Imposter Acceptance Rate, or P(IA), as a locus of points determined by different choices for the decision criterion C as was indicated in FIG. 6. These two figures are only theoretical in order to clarify the nature of the decision problem; as drawn, they imply far greater uncertainty than actually exists for this biometric recognition system.

Equation (14) tells us that the strategy curve shown in FIG. 7 will always lie above the diagonal line in this probability space. In general, one would like to use decision strategies that generate points as close as possible to the upper left corner, since reaching that ideal would mean that all authentics were accepted while all imposters were rejected. Clearly, strategies that are excessively conservative or excessively liberal correspond to sliding along the curve towards the two diagonal extremes, in which all Subjects, authentics and imposters alike, are either universally rejected (lower left) or universally accepted (upper right). Clearly the Identification Power in FIG. 7 would thus be zero anywhere along the diagonal, and it would equal one in the upper left corner of this space. The overall power of a detection method, regardless of where one chooses to place the decision criterion along the liberal— conservative strategy curve, may therefore be gauged by the length of the line segment joining the diagonal line and the bend in the strategy curve, i.e., the length of the "arrow" in the "bow".

Having formulated the biometric identification problem within a framework of signal processing and statistical decision theory, we can now evaluate the identifiability of persons by their irises.

The distribution of Hamming distances computed among 2,064 pairs of different irises (labelled "imposters" because no pair came from the same person) was seen previously in FIG. 5. As expected, the average Hamming distance is 0.5, since any bit in the 2,048-bit (256-byte) codes for two different irises has equal probability of agreeing or disagreeing. The distribution of Hamming distances is tightly clustered around the expected value; the actual means is $\mu=0.497$ with $\sigma=0.038$ standard deviation.

Figure 8:
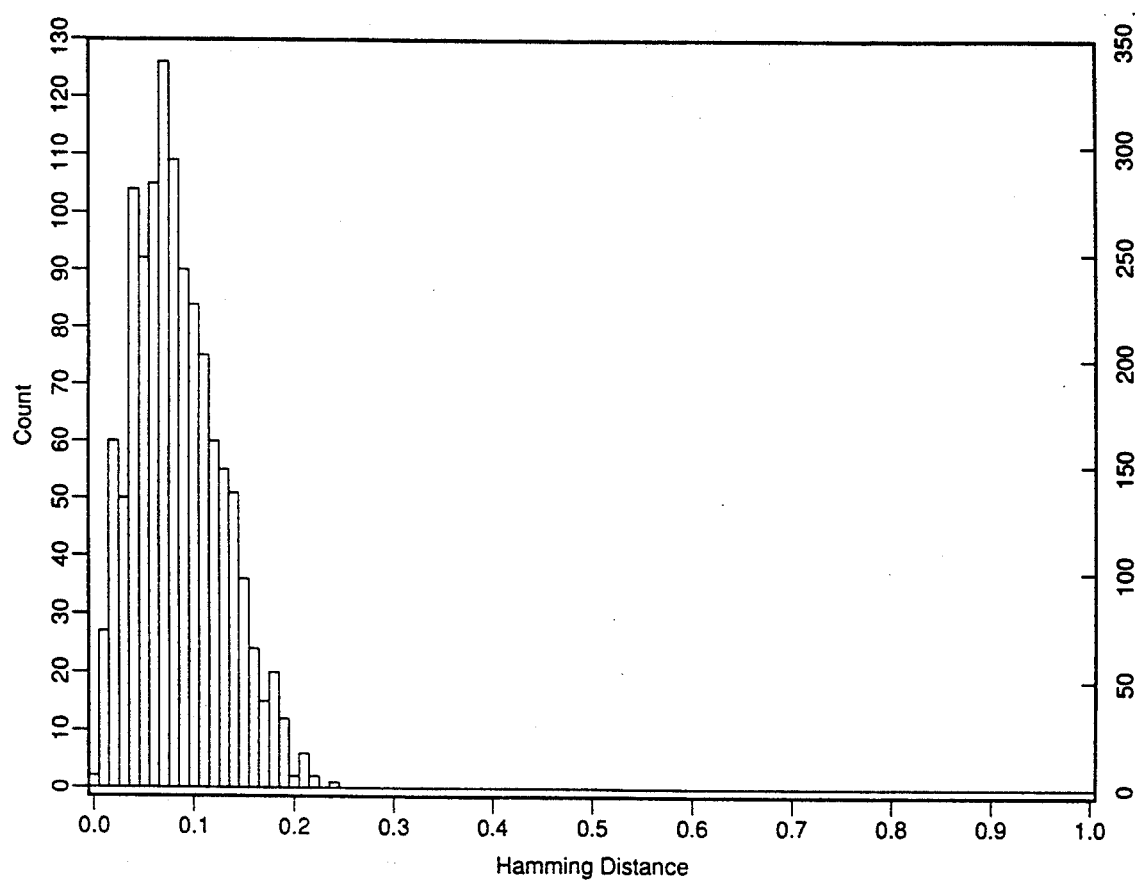
FIG. 8 is a plot showing the Hamming distances for "authentics", i.e., for comparisons between iris codes computed on different occasions from the same iris.

FIG. 8 shows the distribution of Hamming distances computed among 1,228 pairs of different pictures of the same iris ("authentics"), obtained at different times. Ideally these Hamming distances should be zero, if the images were truly identical; however, differences in angle of gaze, partial eyelid closure, specular reflections in the iris, and relative constriction of the pupil, generate some differences in the structure encoded. Nonetheless, these Hamming distances are clearly substantially smaller than those seen in FIG. 5 for imposters. The authentics distribution has a mean of $\mu=0.084$ with $\sigma=0.0435$ standard deviation.

Because of the possible variation in the tilt of a person's head on different occasions, together with cyclovergence (torsional rotation) of the eye in its socket, it is necessary to carry out all iris code comparisons over a range of different relative orientations. Only the best match obtained from a set of such comparisons is kept as the measure of similarity. Because such a "best of n relative orientations" test always selects the lowest Hamming distance, both for comparisons of authentics and imposters, both of these distributions are shifted towards the left and are made narrower than they would be otherwise. Of course, this does not affect the nature of the decision task, which is not based on any assumptions about the forms of the two distributions. But it improves overall decision performance, since the degree of match between different images of the same eye benefits much more from comparing them at several candidate relative orientations, than does the match between codes for unrelated irises.

Figure 9:
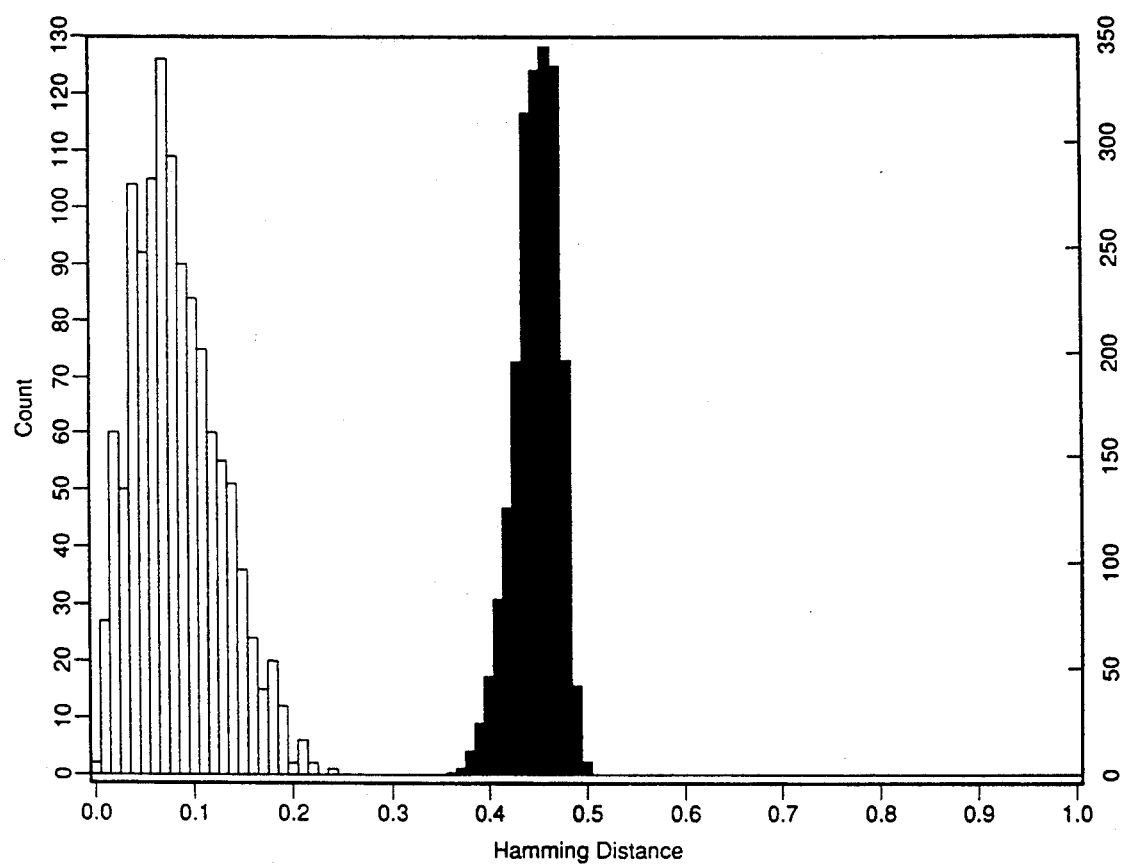
FIG. 9 is a plot showing Hamming distances for authentics and imposters, combined.

The authentics distribution seen in FIG. 8 was obtained with the best of 7 orientations rule. FIG. 9 shows this distribution in conjunction with the corresponding distribution for imposters, which compares the same set of 2,064 unrelated iris codes as was used for FIG. 5 but now using the same new "best of 7 orientations" rule. These two distributions have no empirical overlap. FIG. 10 shows the same pair of histograms fitted by theoretical bionomial distributions, whose parameters are fitted to match the means and variances of the observed pair of empirical distributions. The binomial form is mathematically appropriate, given the nature of the code comparisons process as a statistical sequence of Bernoulli (coin-tossing) trials. The problem of iris pattern recognition is thereby transformed essentially into a statistical test of independence. The Exclusive-OOR test between iris code bits examines the hypothesis that the two code sequences could have risen from independent random processes. This test of statistical independence is failed almost certainly for two codes arising from the same eye, but it is passed almost certainly for two codes arising from different eyes.

Figure 11:
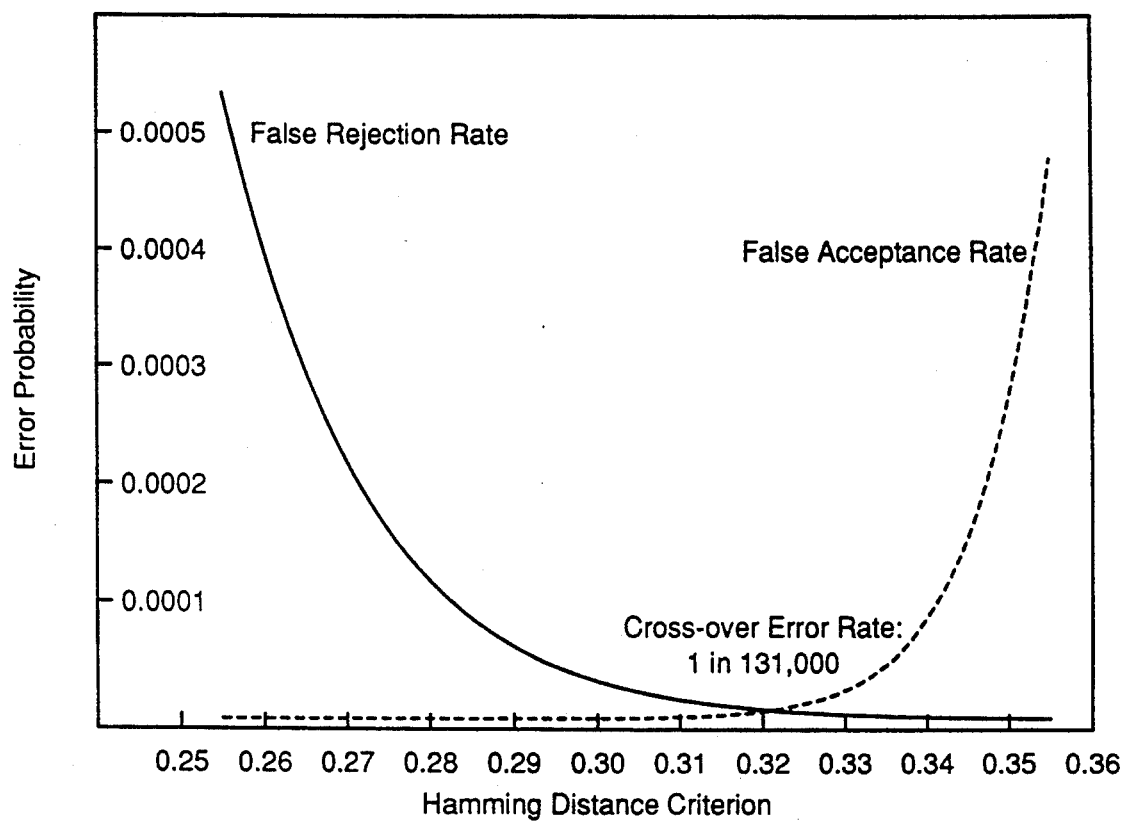
FIG. 11 is a plot of error as a function of Hamming distance criterion.

Although the two empirical distributions seen in FIG. 9 have no overlap, and indeed there were no observed points falling in the range of 0.25 to 0.35 Hamming distance, theoretically there would have been some overlap between the two distributions if a large enough database had been studied. The fitted pair of theoretical binomial curves superimposed in FIG. 10 provides a way to estimate the error rates if there had been an unlimited number of observations. These overlapping fitted distributions should be considered with FIG. 6 in mind, which introduced the basic framework for statistical decision-making. As specified in Equations (8)–(11), the probabilities of personal identity or non-identity, and the predicted error rates, can be calculated as the cumulative integrals under these two distributions on either side of any chosen Hamming distance decision criterion. The error rates for falsely accepting imposters (IAR) and rejecting authentics (APR), in the observed population of 1,208 paired comparisons, are plotted in FIG. 11 as a function of Hamming distance criterion. This graph makes explicit the trade-off between Type I and Type II error rates (IAR and ARR), which can be manipulated by changes in criterion. Their theoretical cross-over point occurs for a Hamming distance criterion of about 0.321, at which point the probabilities of false acceptance and false rejection are both 1 in 131,000. For situations demanding a much more conservative decision criterion, such as for example a Hamming distance of 0.26, for which the chances of imposter acceptance are around one in two billion, FIG. 11 shows that the rate of correctly accepting authentics is still higher than 99.96%. The dotted curves are the theoretical error rates computed according to Equations (7) and (8), using the fitted binomial distributions for $P_{Au}(H)$ and $P_{Imp}(H)$ seen in FIG. 10.

The binomial framework developed earlier for this statistical pattern recognition task allows us to compute the confidence levels associated with any decision confirming or disconfirming a person's identity on the basis of their iris signature. Specifically, when two iris codes are compared, e.g., a previously "enrolled" one and a presenting one, and their Hamming distance is measured, we can calculate the odds that a Hamming distance of this size or smaller might have arisen by chance from two different irises. Only if this probability is sufficiently small would the person be accepted as authentic.

The confidence level associated with the decision requires summing over all possible combinations $$\binom{N}{m}$$

of the N (=173) independent binary degrees-of-freedom in which there are $m \leq CN$ bits mismatching (resulting in a Hamming Distance HD less than or equal to the fraction C of mismatches), times the probability of each such event, given that p is the probability (0.5) that a pair of bits do not match and q is the probability that they do match:

$$P(HD \leq C) = \sum_{m=1}^{CN} \binom{N}{m} (p)^m (q)^{N-m} \qquad (16)$$

Equation (16) specifies the probability that the Hamming distance HD between codes for different irises might happen by chance to be smaller than a given decision criterion C. This lets us determine, for any given decision criterion, what would be the odds against chance for a false acceptance. (Stirling's approximation allows estimates of the large factorials needed to evaluate Equation 16.) As tabulated in FIG. 12, these theoretical odds are roughly one in 2.4 million for a Hamming distance criterion of 0.30, and the odds rapidly reach "planetary" levels (in the billions) for criteria of 0.26 or smaller. Obviously, such improbable errors when using such criteria never occurred in the existing data base. Indeed, the imposter acceptance rate observed among the 2,064 iris code comparisons was already at zero for a Hamming distance criterion as high as 0.35, at which point the authentic acceptance rate was about one in a million (bottom row of FIG. 12).

A final gauge of the power of the present biometric signature security system is the computed confidence level associated with typical, or average, Hamming distances encountered among different pictures of the same iris. As was apparent in the histograms of FIGS. 8 and 9, the average Hamming distance between two iris codes generated from the same iris was 0.084. For this typical case, the confidence level for a decision to accept the individual as authentic is truly astronomical. Specifically, the odds that a Hamming distance of this average size or smaller could arise from an imposter, according to Equation (16), are one in $10^{31}$.

The analysis performed by this embodiment of the present invention generates an identification code of 256 bytes of data (2048 bits). This number has been found to yield a reliable identification code, combined with optimized processing characteristics. The iris code maps all different irises into a universal, abstract mathematical code of fixed length. This allows code comparisons to be made extremely efficiently, even between relatively "featureless" irises (perhaps as the result of low contrast imaging), and those imaged with rich visible texture.

The comparison process lends itself directly to simple hardware implementation based on the XOR-gate. Built from just three transistors, XOR gates are available in standard semiconductor chips. For example, the standard IC, named 74F86, contains four independent XOR gates which can operate at 80 Megahertz, and only costs a few cents. Any comparison between two iris codes, as well as exhaustive searches through large databases of stored iris codes, can be implemented extremely rapidly and with inherent parallelism. For example, a circuit board containing a $32 \times 16$ array of 74F86 ICs, could exhaustively compare a "presenting" iris code against a population of 80 million previously stored iris codes within one second, to establish reliably whether the individual is any one of those persons.

Because each bit in the code can be regarded as a binary random variable, the theory of binomial statistics has been applied to evaluate the probability of any given fraction of the bits in two different iris codes agreeing just by chance. This permits the objective calculation of confidence levels for every decision, using statistical decision theory. Insofar as the pattern recognition problem has been converted here into a statistical test on the polarities of Gabor coefficients computed over multiple scales of analysis in a dimensionless coordinate system, the overall theoretical basis of the present invention can be regarded as a synthesis of unique signal processing methods with statistical decision theory.

It is understood that the above-described embodiment is merely illustrative of the application. Other embodiments may be readily devised by those skilled in the art which will embody the principles of the invention and fall within the spirit and scope thereof.

I claim:

1. A method for uniquely identifying a particular human being by biometric analysis of the iris of the eye, comprising the following steps:
   acquiring an image of an eye of the human to be identified;
   isolating and defining the iris of the eye within the image, wherein said isolating and defining step includes the steps of:
      defining a circular pupillary boundary between the iris and pupil portions of the image;
      defining another circular boundary between the iris and sclera portions of the image, using arcs that are not necessarily concentric with the pupillary boundary;
      establishing a polar coordinate system on the isolated iris image, the origin of the coordinate system being the center of the circular pupillary boundary, wherein the radial coordinate is measured as a percentage of the distance between the said circular pupillary boundary and said circular boundary between the iris and sclera; and
      defining a plurality of annular analysis bands within the iris image;
   analyzing the iris to generate a presenting iris code;
   comparing said presenting code with a previously generated reference iris code to generate a measure of similarity between said presenting iris code and said reference code;
   converting said similarity measure into a decision that said iris codes either do or do not arise from the same iris; and
   calculating a confidence level for the decision.

2. The method of claim 1, wherein:
   said analysis bands exclude certain preselected portions of the iris image likely to be occluded by the eyelids, eyelashes, or specular reflection from an illuminator.

3. The method of claim 2, wherein said analyzing step includes the steps of:

analyzing the portion of the iris image lying within said annular analysis bands and employing signal processing means to generate an iris code for said iris image portion.

4. The method of claim 3, wherein:

said signal processing means comprises applying multi-scale, self-similar, two dimensional quadrature bandpass filters in polar coordinates to the iris image.

5. The method of claim 4, wherein:

said iris code has a fixed number of bits and a universal format for all irises.

6. The method of claim 5, wherein said analysis step includes:

applying said bandpass filters to a region of the raw iris image signal to remove luminance bias, to remove slow luminance gradients arising from oblique illumination, and to remove noise, and to prevent aliasing.

7. The method of claim 6, wherein:

the value of each bit in the iris code is specified as a "1" or "0", by computing over whatever region of the iris constitutes the support for the said filters of a given size at a given location, the most-significant-bit of the filtered outputs according to the following definitions:

$$MSB_{Re}(r,\theta) = 1 \text{ if}$$
$$Re \int_\rho \int_\phi e^{-2\pi i\omega(\theta-\phi)} e^{-(r-\rho)2/\alpha^2} e^{-(\theta-\phi)2/\beta^2} I_-(\rho,\phi) \, \rho d\rho d\phi > 0$$

$$MSB_{Re}(r,\theta) = 0 \text{ if}$$
$$Re \int_\rho \int_\phi e^{-2\pi i\omega(\theta-\phi)} e^{-(r-\rho)2/\alpha^2} e^{-(\theta-\phi)2/\beta^2} I_-(\rho,\phi) \, \rho d\rho d\phi \leq 0$$

$$MSB_{Re}(r,\theta) = 1 \text{ if}$$
$$Im \int_\rho \int_\phi e^{-2\pi i\omega(\theta-\phi)} e^{-(r-\rho)2/\alpha^2} e^{-(\theta-\phi)2/\beta^2} I_-(\rho,\phi) \, \rho d\rho d\phi > 0$$

$$MSB_{Re}(r,\theta) = 0 \text{ if}$$
$$Re \int_\rho \int_\phi e^{-2\pi i\omega(\theta-\phi)} e^{-(r-\rho)2/\alpha^2} e^{-(\theta-\phi)2/\beta^2} I_-(\rho,\phi) \, \rho d\rho d\phi \leq 0$$

8. The method of claim 7, wherein said comparing step includes the steps of:

comparing any two iris codes by computing the elementary logical XOR (exclusive-OR logical operation) between all their corresponding bits; and computing the squared norm of the resulting binary vector;

wherein this comparison measure is defined as the Hamming distance between the two iris code vectors.

9. The method of claim 8, further comprising:

repeating the comparing step for several different relative shifts of the iris code along its angular axis, to compensate for possible tilt of the head of the presenting subject or torsional eye rotation.

10. The method of claim 9, wherein said calculating step includes the steps of:

converting said Hamming distance into a calculated likelihood that the two codes originated from the same iris, and hence the same person.

11. The method of claim 10, wherein:

said calculated likelihood is found by computing the probability that an observed matching fraction of bits in the presenting code and reference code could match by chance if the codes were independent, i.e., arising from separate irises.

12. The method of claim 11, wherein:

the measured Hamming distance is converted into a probability that the two said iris codes are from the same eye;

a preselected criterion is applied to said measured Hamming distance to generate a "yes" or "no" decision; and a confidence level for the decision is provided by the calculated probability.

13. The method of claim 12, wherein:

said circular pupillary boundary is defined by the relationship:

$$\max_{(r,x_0,y_0)} \left| \left| \frac{\partial}{\partial r} \phi_{r,x_0,y_0} I(x,y) ds \right| \right|$$

where r is the radius of said boundary, $x_0$ and $y_0$ are center coordinates, and I is image intensity;

wherein said radius and center coordinates are varied in a preselected pattern.

14. The method of claim 13, wherein:

said other circular boundary between the iris and sclera portion of the image is defined by determining the distances from said coordinate system origin to the left and right limbus in accordance with the following relationship:

$$\max_{r\in[1.5r_0,10r_0]} \frac{\partial}{\partial r} \int_{\rho=r-\delta}^{r+\delta} \frac{2}{\pi\delta r} \int_{\theta=\phi-\pi/8}^{\phi+\pi/8} I(\rho,\theta) \rho d\rho d\theta$$

where r is the pupillary radius previously defined, $\delta$ is a radial shell distance, $I(\rho,\theta)$ is the original image intensity in polar coordinates, and $\phi$ equals 0 or $\pi$ in order to find the limbus in the 3-o'clock or 9-o'clock meridia, respectively.

15. The method of claim 14, wherein:

said analysis bands include a plurality of annular bands extending completely around said pupil, and a plurality of semi-annular bands extending from polar angles of approximately 45 degrees to 135 degrees and from 225 degrees to 315 degrees around said pupil.

16. The method of claim 15, wherein:

said analysis bands are spaced at equal fractional radial distances from an inner point located at a preselected fractional distance from said pupillary boundary to an outer point located at preselected fractional distance from said limbus, said spacing being angularly weighted to account for said difference between fractional distances from said coordinate center to said right and left limbi.

17. The method of claim 12, wherein:

said bandpass filters are 2-D Gabor filters.

18. The method of claim 17, wherein:

said 2-D Gabor filters are defined in polar coordinates as follows:

$$G(r,\theta) = e^{2\pi i\omega(\theta-\theta 0)} e^{-(r-r0)2/\alpha^2} e^{-(\theta-74))2/\beta^2}$$

where r is radius, $\theta$ in angular distance in radians, $\omega$ is frequency, and $\alpha$ and $\beta$ are constants.

19. The method of claim 18, wherein:

said iris code is comprised of 2048 bits.

20. The method of claim 1, wherein:

said circular pupillary boundary is defined by the relationship:

$$\max_{(r,x_0,y_0)} \left\| \frac{\partial}{\partial r} \phi_{r,x_0,y_0} I(x,y) ds \right\|$$

where r is the radius of said boundary, $x_0$ and $y_0$ are center coordinates, and I is image intensity;

wherein said radius and center coordinates are systematically varied by iterative gradient ascent to find the maximum in said defined relationship.

21. The method of claim 20, wherein:

said other circular boundary between the iris and sclera portion of the image is defined by determining the distances from said coordinate system origin to the left and right limbus in accordance with the following relationship:

$$\max_{r \in [1.5r_0, 10r_0]} \frac{\partial}{\partial r} \int_{\rho=r-\delta}^{r+\delta} \frac{2}{\pi \delta r} \int_{\theta=\phi-\pi/8}^{\phi+\pi/8} I(\rho,\theta) \rho \, d\rho \, d\theta$$

where $r_0$ is the pupillary radius previously defined, $\delta$ is a radial shell distance, $I(\rho,\theta)$ is the original image intensity in polar coordinates, and $\phi$ equals 0 or $\pi$ in order to find the limbus in the 3-o'clock or 9-o'clock meridia, respectively.

* * * * *